(12) United States Patent
Goto et al.

(10) Patent No.: US 6,794,480 B2
(45) Date of Patent: Sep. 21, 2004

(54) MONOMER CONTAINING ELECTRON-WITHDRAWING GROUP AND ELECTRON-DONATIVE GROUP, AND COPOLYMER AND PROTON-CONDUCTIVE MEMBRANE COMPRISING SAME

(75) Inventors: Kohei Goto, Ibaraki (JP); Masayuki Takahashi, Ibaraki (JP); Yoshitaka Yamakawa, Ibaraki (JP); Makoto Higami, Ibaraki (JP)

(73) Assignee: JSR Corporation, Tokyo (JP)

( * ) Notice: Subject to any disclaimer, the term of this patent is extended or adjusted under 35 U.S.C. 154(b) by 158 days.

(21) Appl. No.: 10/105,316

(22) Filed: Mar. 26, 2002

(65) Prior Publication Data

US 2002/0177656 A1 Nov. 28, 2002

(30) Foreign Application Priority Data

Mar. 30, 2001 (JP) .................................... P.2001-099523

(51) Int. Cl.$^7$ .......................... C08G 14/00; C08G 8/02
(52) U.S. Cl. ..................... 528/125; 528/86; 528/171; 528/255; 528/211; 528/219; 528/373; 528/242; 528/288; 528/291; 528/293
(58) Field of Search .......................... 528/125, 86, 171, 528/205, 211, 219, 373; 525/242, 288, 291, 293

(56) References Cited

U.S. PATENT DOCUMENTS 6,084,053 A     7/2000  Matsubara et al.
6,300,465 B1   10/2001  Akiike et al.

FOREIGN PATENT DOCUMENTS

EP            1245554        * 10/2002

* cited by examiner

Primary Examiner—Duc Truong
(74) Attorney, Agent, or Firm—Oblon, Spivak, McClelland, Maier & Neustadt, P.C.

(57) ABSTRACT

A monomer containing an electron-withdrawing group and an electron-donative group which can be easily controlled in the upper limit of the amount of a sulfonic acid, which impairs the mechanical properties of a copolymer, and can provide a sulfonated polymer that forms a proton-conductive membrane having a high proton conductivity over a wide temperature range, an excellent mechanical strength and an excellent proton conductivity and showing inhibited swelling in hot water and an aqueous solution of methanol, and a copolymer obtained from the monomer. A monomer containing an electron-withdrawing group and an electron-donative group represented by the following general formula (1):

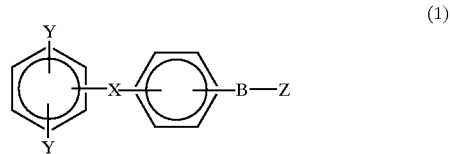

(1)

wherein Y represents a iodine atom, chlorine atom or bromine atom; X represents an electron-withdrawing group; B represents an electron-donative group; and Z represents an aryl group having a specific structure or a monovalent condensed ring hydrocarbon group such as naphthyl group.

14 Claims, 3 Drawing Sheets

MONOMER CONTAINING ELECTRON-WITHDRAWING GROUP AND ELECTRON-DONATIVE GROUP, AND COPOLYMER AND PROTON-CONDUCTIVE MEMBRANE COMPRISING SAME

FIELD OF THE INVENTION

The present invention relates to a monomer containing an electron-withdrawing group and an electron-donative group and a copolymer comprising and a proton-conductive membrane comprising same. More particularly, the present invention relates to a polyarylene-based copolymer useful as a proton-conductive membrane which can be used as electron for primary battery, electrolyte for secondary battery, high molecular solid electrolyte for fuel cell, display element, sensor, signal transfer medium, solid capacitor, ion exchange membrane, etc., a monomer to be used for the copolymer, and a proton-conductive membrane comprising the copolymer.

DESCRIPTION OF THE RELATED ART

Electrolytes are usually used as (aqueous) solutions in many cases. In recent years, however, there is a growing tendency to replace such aqueous soluble-form electrolytes with solid electrolytes. The first reason for this is the easiness of processing in applications of solid electrolytes to, e.g., the electrical/electronic materials mentioned above. The second reason is the trend toward reduction in weight, thickness, length and size, and toward energy saving.

Conventionally known proton-conductive materials include both inorganic materials and organic materials. Examples of the inorganic materials include uranyl phosphates which form hydrate. However, these inorganic compounds are insufficient in interfacial contact to pose many problems concerning the formation of a conductive layer on a substrate or electrode.

On the other hand, examples of the organic compounds include organic polymers such as polymers belonging to the so-called cation-exchange resins, e.g., sulfonated vinyl polymers such as sulfonated polymers with perfluoroalkylsulfonic acid represented by Nafion (manufactured by E. I. Du Pont de Nemours & Co., Inc.), and perfluoroalkylcarboxylic acid polymers, and polymers prepared with incorporating sulfonic acid groups or phosphoric acid groups into heat-resistant polymers such as polybenzimidazole and poly (ether-ether-ketone)s [see *Polymer Preprints*, Japan, Vol.42, No. 7, pp. 2490–2492 (1993); *Polymer Preprints*, Japan, Vol. 43, No. 3, pp. 735–736 (1994); and *Polymer Preprints*, Japan, Vol. 42, No. 3, p. 730 (1993)].

These organic polymers are usually used in the form of a membrane. A conductive membrane made of these organic polymers can be bonded to an electrode while taking advantage of the solvent solubility or thermoplasticity. However, many of these organic polymers have the following problems besides being still insufficient in proton conductivity. The organic polymers deteriorate in durability or in proton conductivity at elevated temperatures (100° C. or higher). The organic polymers show drastic deterioration of dynamic properties, particularly elastic modulus. The organic polymers have a great dependence on humidity conditions. Further, the adhesion of the organic polymers to the electrode is not fully satisfactory. Moreover, the conductive membrane swells excessively during operation due to the hydrophilic polymer structure, and this swelling leads to a decrease in strength properties or a deformation. Consequently, application of those organic polymers to the aforementioned electrical/electronic materials and the like pose various problems.

U.S. Pat. No. 5,403,675 proposes a solid polymer electrolyte comprising a sulfonated rigid polyphenylene. This polymer is produced from a polymer comprising a phenylene chain obtained by polymerizing an aromatic compound (the polymer structure is described in column 9 in the specification) by reacting the phenylene polymer as the main component with a sulfonating agent to incorporate sulfonic acid groups thereinto. However, the incorporation of a large amount of sulfonic acid groups results in a sulfonated polymer having considerable deterioration in mechanical properties that exhibits a deteriorated toughness and thus can crack although proton conductivity improves with the increasing amount of sulfonic acid groups incorporated. Therefore, it is necessary for the polymer to have a desired toughness, maintain proper mechanical properties and be adjusted to a proper sulfonation that realizes a desired proton conductivity. In fact, this polymer undergoes sulfonation too much and thus can be very difficult to have a proper control over the amount of sulfonic acid group to be incorporated therein.

SUMMARY OF THE INVENTION

The invention has been made under these technical circumstances.

Accordingly, one object of the invention is to provide a polyarylene-based copolymer which can be easily controlled in the upper limit of the amount of a sulfonic acid, which impairs the mechanical properties of a copolymer, and can provide a sulfonated polymer that forms a proton-conductive membrane having a high proton conductivity over a wide temperature range, an excellent mechanical strength and an excellent proton conductivity and showing inhibited swelling in hot water and an aqueous solution of methanol.

Another object of the invention is to provide a novel monomer to be used in the copolymer.

Still another object of the invention is to provide a proton-conductive membrane comprising the copolymer.

The foregoing aim of the invention will become apparent from the following detailed description and examples.

The invention provides a monomer containing an electron-withdrawing group and an electron-donative group represented by the following formula (1):

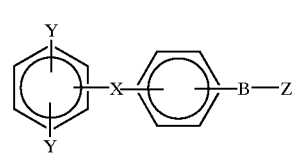

(1)

wherein Y represents a iodine atom, chlorine atom or bromine atom; X represents an electron-attractive group; B represents an electron-donative group; and Z represents a group represented by the following formula (2-1) or (2-2) or a monovalent condensed ring hydrocarbon group:

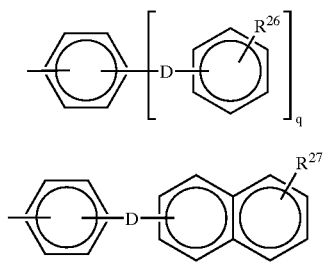

(2-1)

(2-2)

wherein D represents an electron-donative group or single bond; $R^{26}$ and $R^{27}$ each represent a hydrogen atom, alkyl group or aryl group; and q represents an integer of from 1 or 2.

The monomer represented by the formula (1) is preferably 2,5-dichloro-4'-(4-phenoxyphenoxy)benzophenone.

The invention also provides a copolymer containing a repeating structural unit represented by the following formula (3) (hereinafter referred to as "repeating structural unit (3)") in an amount of from 5 to 95 mol % and having a weight average molecular weight of from 10,000 to 1,000,000:

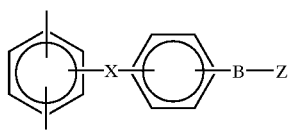

(3)

wherein X, B and Z are the same as defined in the formula (1) above.

The copolymer of the invention preferably contains a repeating structural unit having a flexible structure in its main chain other than the repeating structural unit represented by the above formula (3) in an amount of from 5 to 95 mol %.

The copolymer of the invention may further contains a sulfonic acid group in an amount of from 0.5 to 3 mg equivalents/g.

The invention further provides a proton-conductive membrane comprising the above-described copolymer containing a sulfonic acid group.

BRIEF DESCRIPTION OF THE DRAWINGS

By way of example and to make the description more clear, reference is made to the accompanying drawings in which.

DETAILED DESCRIPTION OF THE INVENTION

Monomer (1)

Figure 1:
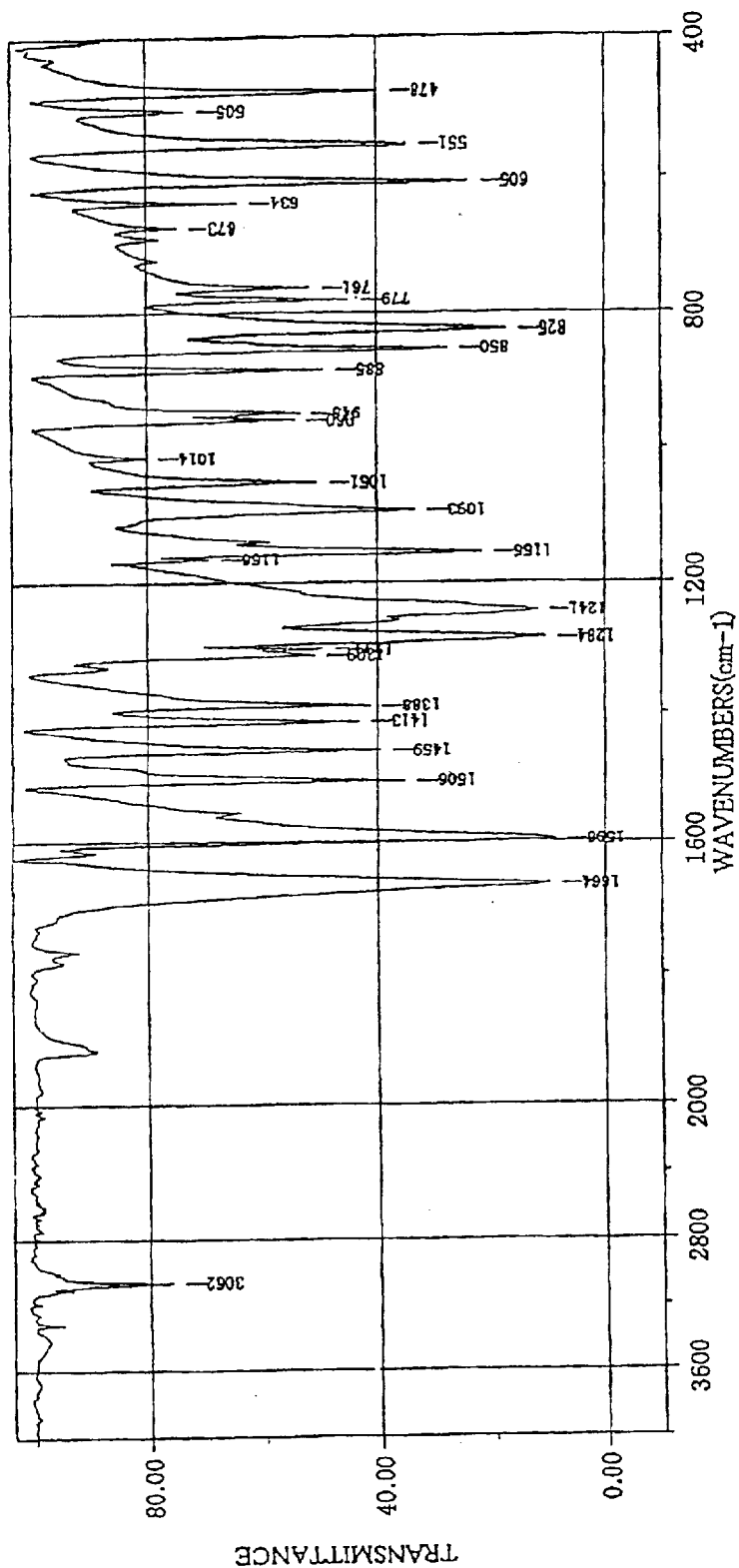
FIG. 1 is the infrared absorption spectrum of 2,5-dichloro-4'-fluorobenzophenone obtained in Synthesis Example 1.

The monomer (1) of the invention is a compound containing an electron-withdrawing group and an electron-donative group represented by the formula (1) described above.

In the formula (1), Y represents a chlorine atom, bromine atom or iodine atom.

In the formula (1), X represents an electron-withdrawing group such as —CO—, —CONH—, —(CF$_2$)$_p$— (in which p represents an integer of from 1 to 10), —C(CF$_3$)$_2$—, —COO—, —SO— and —SO$_2$—.

In the formula (1), B represents an electron-donative group such as —O—, —S—, —CH=CH—, —C≡C— and group represented by the following formula:

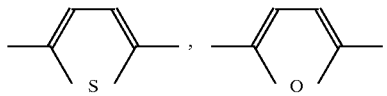

In the formula (1), Z represents a group represented by the formula (2-1) or (2-2) described above or a monovalent condensed ring hydrocarbon group.

Examples of the alkyl group represented by $R^{26}$ or $R^{27}$ in the formulae (2-1) and (2-2) include methyl group, and ethyl group. Examples of the aryl group represented by $R^{26}$ or $R^{27}$ in the formulae (2-1) and (2-2) include phenyl group, naphthyl group, and anthranyl group. Examples of the monovalent condensed ring hydrocarbon group represented by Z include naphthyl group, and anthranyl group. The suffix q represents an integer of 1 or 2.

Examples of the monomer (1) of the invention include the following compounds.

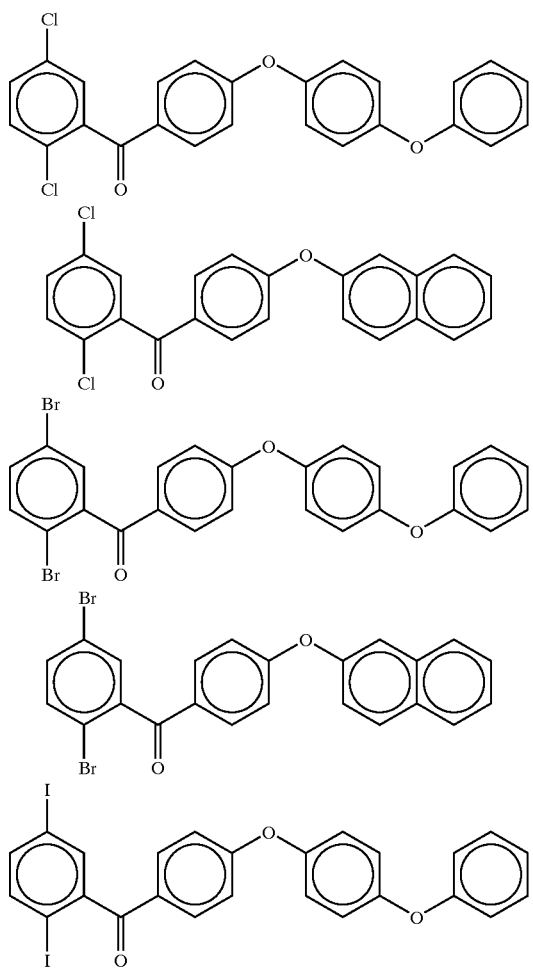

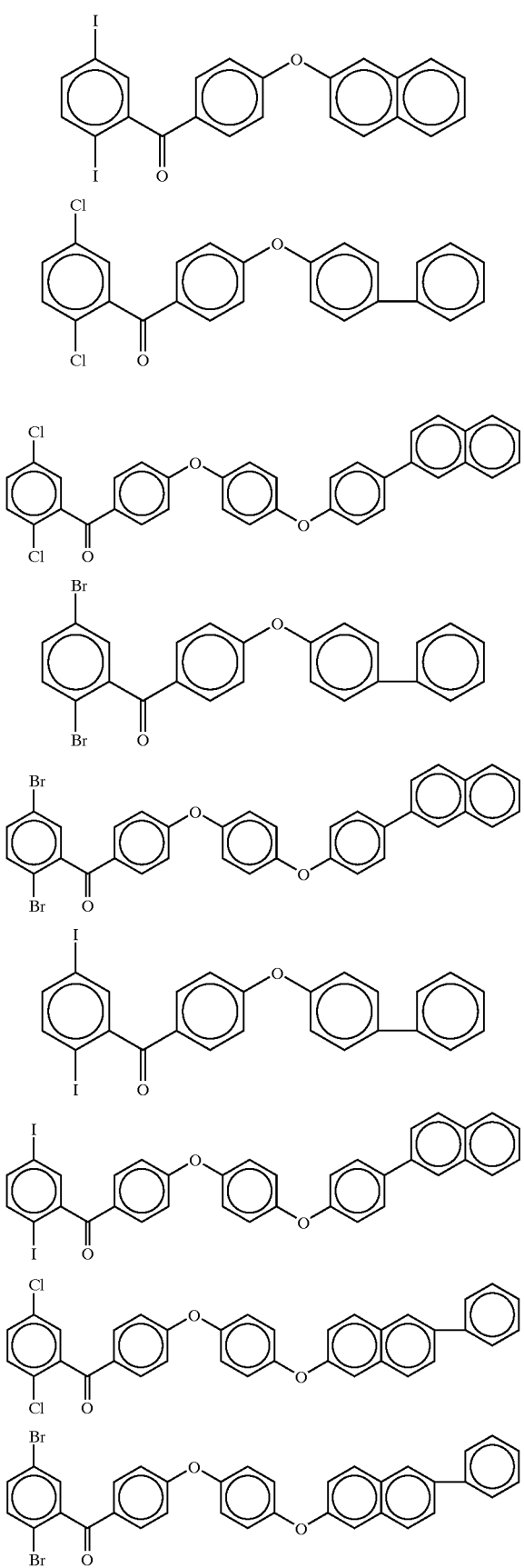

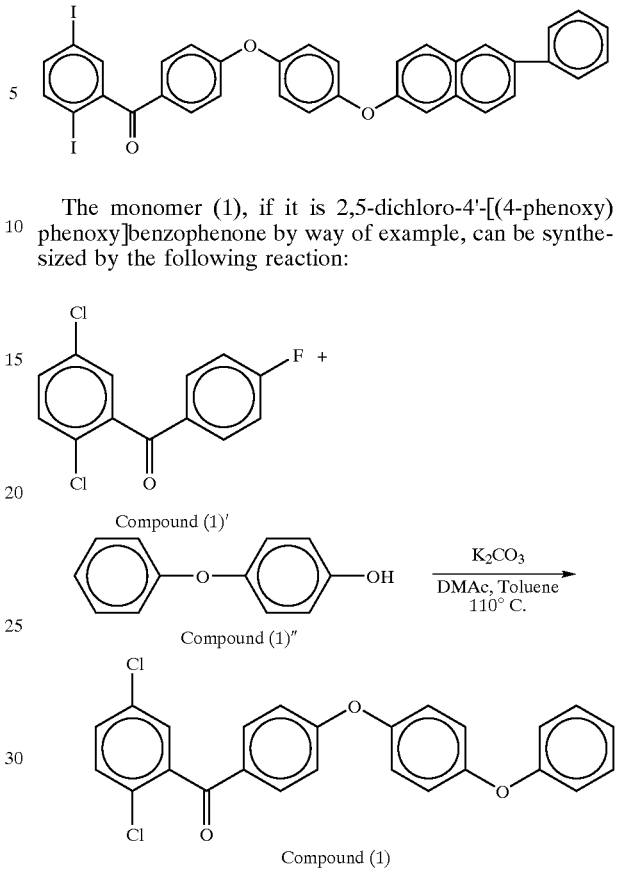

Compound (1)

The monomer (1), if it is 2,5-dichloro-4'-[(4-phenoxy)phenoxy]benzophenone by way of example, can be synthesized by the following reaction:

In some detail, to Compound (1)' 2,5-dichloro-4"-fluorobenzophenone and Compound (1)" phenoxyphenol are added potassium carbonate to produce a highly reactive phenoxide which is then reacted at a temperature of from 80° C. to 200° C. in the presence of an aprotic dipolar solvent such as dimethylacetamide, N-methylpyrrolidone and dimethylsulfoxide as a reaction solvent for 1 to 30 hours to obtain Compound (1) 2,5-dichloro-4'-[(4-phenoxy)phenoxy]-benzophenone. In this case, as an azeotropic solvent for removing the resulting condensate water from the reaction system there may be used a solvent which undergoes azeotropy with water such as benzene, toluene, xylene, cumene, ethylbenzene, cyclohexane, hexane, heptane, octane, nonane, decane and decahydronaphthalene.

The proportion of Compound (1)' and Compound (1)" is normally substantially equimolecular. The molar ratio of Compound (1)'/Compound (1)" is from 1.25/1.00 to 1.00/1.25.

The monomer (1) of the invention thus obtained (e.g., Compound (1)) can be then identified for its structure by IR, NMR, elementary analysis, etc.

Copolymer

The copolymer of the invention contains the repeating structural unit represented by the formula (3) in an amount of from 5 to 95 mol %, preferably from 10 to 80 mol %, more preferably from 15 to 75 mol %, and has a weight average molecular weight of from 10,000 to 1,000,000, more preferably from 20,000 to 800,000.

The repeating structural unit (3) comprises the monomer (1) of the invention as an essential component.

In the copolymer of the invention, the repeating structural unit other than the repeating structural unit (3) (hereinafter referred also to as "other repeating structural unit") is preferably a repeating structural unit having a flexible structure in its main chain (hereinafter referred also to as "unit (A)"), optionally other repeating structural units (hereinafter referred also to as "unit (B)") in addition thereto.

Referring to the proportion of the repeating structural unit (3) and the other repeating structural units, the proportion of the repeating structural unit (3) is from 5 to 95 mol %, preferably from 10 to 80 mol %, more preferably from 15 to 75 mol %, and the proportion of the other repeating structural units is from 5 to 95 mol %, preferably from 20 to 90 mol %, more preferably from 25 to 85 mol %. When the proportion of the repeating structural unit (3) falls below 5 mol %, the amount of the sulfonic acid group is not great enough to allow the sulfonic acid group in the sulfonated polymer thus obtained to show a desired proton conductivity. On the contrary, when the proportion of the repeating structural unit (3) exceeds 95 mol %, the subsequent copolymerization has no effect of improving mechanical properties, water resistance and methanol resistance and controlling the upper limit of the amount of sulfonic acid group to be incorporated.

Among the other repeating structural units, the unit (A) may be an aromatic compound unit represented by the following formula (4). As the unit (B) there may be used at least one of the aromatic compound units represented by the following formulae (5) to (7).

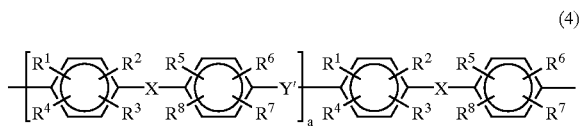

(4)

wherein X represents an electron-withdrawing group; Y' represents an electron-donative group; a represents an integer of 0 or 1; and $R^1$ to $R^8$ may be the same or different and each represent a sulfonic acid group, hydrogen atom, halogen atom, alkyl group, halogenated alkyl group, allyl group or aryl group.

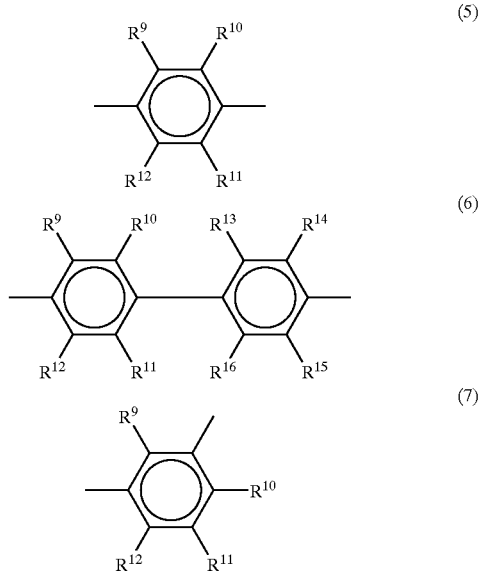

(5)

(6)

(7)

wherein $R^9$ to $R^{16}$ may be the same or different and each represent a hydrogen atom, alkyl group, halogen atom, halogenated alkyl group, aryl group or group represented by the following formula (8):

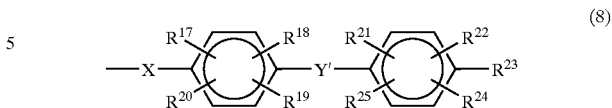

(8)

wherein $R^{17}$ and $R^{25}$ each represent a hydrogen atom, alkyl group, halogen atom, halogenated alkyl group or aryl group; X represents an electron-withdrawing divalent group; and Y' represents an electron-donative divalent group.

The copolymer of the invention comprises the repeating structural unit represented by the formula (3) and the other repeating structural units (e.g., unit (A) and optionally the unit (B)).

The sulfonic acid group-containing copolymer of the invention can be obtained, e.g., by a process which comprises copolymerizing the monomer (1) of the invention, the monomer corresponding to the general formula (4), and optionally the monomer corresponding to at least one selected from the group consisting of the formulae (5) to (7) in the presence of a catalyst containing a transition metal compound, and then sulfonating the copolymer with a sulfonating agent.

The units (A) and (B) as other repeating structural units constituting the copolymer of the invention, the copolymer of the invention, and the sulfonic acid group-containing copolymer obtained by sulfonation will be further described hereinafter.

The unit (A) will be described hereinafter.

The unit (A) is an aromatic compound unit having an electron-withdrawing group and an electron-donative group in its main chain and is represented, e.g., by the formula (4).

In the formula (4), X represents an electron-withdrawing group as defined in the general formula (1) such as at least one divalent electron-withdrawing group selected from the group consisting of —CO—, —CONH—, —(CF$_2$)$_p$—, —C(CF$_3$)$_2$—, —COO—, —SO— and —SO$_2$—. The suffix p in —(CF$_2$)— represents an integer of from 1 to 10, preferably from 2 to 8.

The term "electron-withdrawing group" as used herein is meant to indicate a group which exhibits a Hammett's substituent constant of 0.06 or larger in the m-position of phenyl group or 0.01 or larger in the p-position of phenyl group.

When X is an electron-withdrawing group as defined above, the benzene ring bonded to the electron-withdrawing group does not undergo sulfonation during the sulfonation of the copolymer obtained, preventing the sulfonation of the polymer chain from proceeding too far. Accordingly, the upper limit of the sulfonic acid group to be incorporated can be controlled without having any adverse effect on the mechanical properties of the copolymer obtained. Examples of the electron-donative group represented by Y' include those listed with reference to the electron-donative group in the formula (1).

Examples of the halogen atom represented by $R^1$ to $R^8$ in the general formula (4) include fluorine atom. Examples of the alkyl group represented by $R^1$ to $R^8$ include methyl group, and ethyl group. Examples of the halogenated alkyl group include trifluoromethyl group, and pentafluoroethyl group. Examples of the allyl group represented by $R^1$ to $R^8$ include propenyl group. Examples of the aryl group represented by $R^1$ to $R^8$ include phenyl group, and fluorophenyl group.

The proportion of the unit (A) in the other repeating structural units in the copolymer of the invention is from 10 to 100 mol %, preferably from 20 to 100 mol %. When the proportion of the unit (A) falls below 10 mol %, the amount of the sulfonic acid to be incorporated after polymerization is too great, raising problems in water resistance and mechanical properties.

On the other hand, the unit (B) is an aromatic compound unit comprising a phenylene chain such as at least one selected from the group consisting of those represented by the formulae (5) to (7) described above.

In the formulae (5) to (7), $R^9$ to $R^{15}$ may be the same or different and each represent a hydrogen atom, alkyl group, halogen atom, halogenated alkyl group, aryl group or group represented by the formula (8) described above.

Examples of the alkyl group represented by $R^9$ to $R^{16}$ include methyl group, ethyl group, propyl group, butyl group, amyl group, and hexyl group.

Examples of the halogen atom $R^9$ to $R^{16}$ include chlorine atom, bromine atom, and iodine atom. Examples of the halogenated alkyl group $R^9$ to $R^6$ include trifluoromethyl group, perfluoroethyl group, perfluoropropyl group, perfluorobutyl group, perfluoropentyl group, and perfluorohexyl group.

Examples of the aryl group $R^9$ to $R^{16}$ include phenyl group, tollyl group, and xylyl group.

Examples of the electron-withdrawing group represented by X and the electron-donative group represented by Y' in the group represented by the above formula (8) include those listed with reference to the general formula (1).

Specific examples of the group represented by the formula (8) include 4-phenoxyphenylcarbonyl group.

The copolymer of the invention can be produced, e.g., by the polymerization of a monomer represented by the formula (1), an aromatic compound having an electron-withdrawing group and an electron-donative group in its main chain represented by the formula (4)' (hereinafter referred also to as "monomer (A)") and optionally an aromatic compound comprising a phenylene chain represented by at least one formula selected from the group consisting of the following general formulae (5)' to (7)' (hereinafter referred also to as "monomer (B)") in a solvent in the presence of a catalyst system containing a transition metal compound.

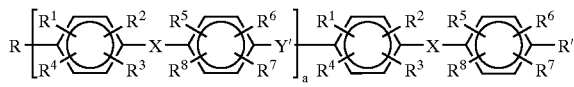

(4)' wherein X, Y' and $R^1$ to $R^8$ are the same as defined in the formula (4); and R and R' may be the same or different and each represent a halogen atom except fluorine atom or a group represented by —$OSO_2Z$ (in which Z represents an alkyl group, halogenated alkyl group or aryl group).

Examples of the group represented by X in the formula (4)' include —CO—, —CONH—, —$(CF_2)_p$— (in which p represents an integer of from 1 to 10), —$C(CF_3)_2$—, —COO—, —SO—, and —$SO_2$—. Examples of the electron-donative group represented by Y' include those listed with reference to the electron-donative group in the formula (1).

Examples of the halogen atom represented by R and R' in the formula (4)' include chlorine atom, bromine atom, and iodine atom. Examples of the alkyl represented by Z in —$OSO_2Z$ in the general formula (1)' include methyl group, and ethyl group. Examples of the halogenated alkyl group represented by Z include trifluoromethyl group. Examples of the aryl group represented by Z include phenyl group, and p-tollyl group.

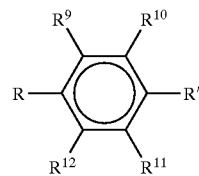

(5)'

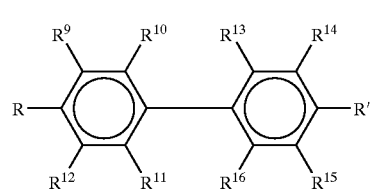

(6)'

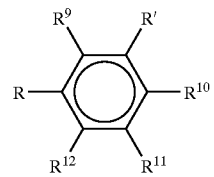

(7)' wherein $R^9$ to $R^{16}$ and R, R' are the same as defined above.

Specific examples of the monomer (A) represented by the formula (4)' include 4,4'-dichlorobenzophenone, 2,4'-dichlorobenzophenone, 3,3'-dichlorobenzophenone, 4,4'-dibromobenzophenone, 2,4'-dibromobenzophenone, 3,3'-dibromobenzophenone, 4,4'-diodobenzophenone, 2,4'-diodobenzophenone, 3,3'-diodobenzophenone, bis(4-trifluoromethylsulfonyloxyphenyl)ketone, bis(3-trifluoromethylsulfonyloxyphenyl)ketone, 4,4'-bis(4-chlorobenzoylamino)diphenyl ether, 4,4'-bis(4-bromobenzoylamino)diphenyl ether, 4,4'-bis(4-iodobenzoylamino)diphenyl ether, 3,4'-bis(4-chlorobenzoylamino) diphenyl ether, 3,4'-bis(4-bromobenzoylamino) diphenyl ether, 3,4'-bis(4-iodobenzoylamino)diphenyl ether, 4,4'-bis(4-chlorobenzoyl) diphenyl ether, 4,4'-bis(4-bromobenzoyl) diphenyl ether, 4,4'-bis(4-iodobenzoyl) diphenyl ether, 3,4'-bis(4-chlorobenzoyl)diphenyl ether, 3,4'-bis(4-bromobenzoyl)diphenyl ether, and 3,4'-bis(4-iodobenzoyl) diphenyl ether.

Specific examples of the monomer (A) represented by the formula (4) include 4,4'-dichlorobenzanilide, 3,3'-dichlorobenzanilide, 3,4'-dichlorobenzanilide, 4,4'-dibromobenzanilide, 3,3'-dibromobenzanilide, 3,4'-dibromobenzanilide, 4,4'-diodobenzanilide, 3,3'-diodobenzanilide, and 3,4'-diodobenzanilide.

Specific examples of the monomer (A) represented by the formula (4)' include bis (chlorophenyl) difluoromethane, bis(chlorophenyl)tetrafluoroethane, bis(chlorophenyl) hexafluoropropane, bis(chlorophenyl)octafluorobutane, bis (chlorophenyl)decafluoropentane, bis(chlorophenyl) dodecafluorohexane, bis (chlorophenyl) tetradecafluoroheptane, bis(chlorophenyl)hexadecafluorooctane, bis (chlorophenyl) octadecafluorononane, bis(chlorophenyl) eisosafluorodecane, bis(bromophenyl)difluoromethane, bis (bromophenyl) tetrafluoroethane, bis(bromophenyl) hexafluoropropane, bis(bromophenyl)octafluorobutane, bis (bromophenyl) decafluoropentane, bis(bromophenyl) dodecafluorohexane, bis(bromophenyl)tetradecafluoroheptane, bis(bromophenyl) hexadecafluorooctane, bis (bromophenyl)octadecafluorononane, bis(bromophenyl)

eicosafluorodecane, bis(iodophenyl) difluoromethane, bis(iodophenyl)tetrafluoroethane, bis(iodophenyl) hexafluoropropane, bis(iodophenyl) octafluorobutane, bis(iodophenyl)decafluoropentane, bis(iodophenyl) dodecafluorohexane, bis(iodophenyl) tetradecafluoroheptane, bis(iodophenyl)hexadecafulorooctane, bis(iodophenyl)octadecafluorononane, and bis(iodophenyl) eicosafluorodecane.

Specific examples of the monomer (A) represented by the formula (4)' include 2,2-bis(4-chlorophenyl) hexafluoropropane, 2,2-bis (3-chlorophenyl)hexafluoropropane, 2,2-bis(4-bromophenyl)hexafluoropropane, 2,2-bis(3-bromophenyl)hexafluoropropane, 2,2-bis(4-iodophenyl) hexafluoropropane, 2,2-bis(3-iodophenyl) hexafluoropropane, bis(4-trifluoromethylsulfonyloxyphenyl)hexafluoropropane, and bis(3-trifluoromethylsulfonyloxyphenyl)hexafluoropropopane.

Specific examples of the monomer (A) represented by the formula (4)' include 4-chlorobenzoic acid-4-chlorophenyl, 4-chlorobenzoic acid-3-chlorophenyl, 3-chlorobenzoic acid-3-chlorophenyl, 3-chlorobenzoic acid-4-chlorophenyl, 4-bromobenzoic acid-4-bromophenyl, 4-bromobenzoic acid-3-bromophenyl, 3-bromobenzoic acid-3-bromophenyl, and 3-bromobenzoic acid-4-bromophenyl.

Specific examples of the monomer (A) represented by the formula (4)' include bis(4-chlophenyl)sulfoxide, bis(3-chlophenyl)sulfoxide, bis(4-bromophenyl)sulfoxide, bis(3-bromophenyl)sulfoxide, bis(4-iodophenyl)sulfoxide, bis(3-iodophenyl)sulfoxide, bis(4-trifluoromethylsulfonyloxyphenyl)sulfoxide, and bis(3-trifluoromethylsulfonyloxyphenyl)sulfoxide.

Specific examples of the monomer (A) represented by the formula (4)' include bis(4-chlorophenyl)sulfone, bis(3-chlorophenyl)sulfone, bis(4-bromophenyl)sulfone, bis(3-bromophenyl)sulfone, bis(4-iodophenyl)sulfone, bis(3-iodophenyl)sulfone, bis(4-trifluoromethylsulfonyloxyphenyl)sulfone, and bis(3-trifluoromethylsulfonyloxyphenyl)sulfone.

Specific examples of the monomer (B) represented by the formula (5)' include 2,5-dichloro-4'-phenoxybenzophenone, p-dichlorobenzene, p-dibromobenzene, p-diiodobenzene, p-dimethylsulfonyloxybenzene, 2,5-dichlorotoluene, 2,5-dibromotoluene, 2,5-diiodotoluene, 2,5-dimethysulfonyloxybenzene, 2,5-dichloro-p-xylene, 2,5-dibromo-p-xylene, 2,5-diodo-p-xylene, 2,5-dichlorobenzotrifluoride, 2,5-dibromobenzotrifluoride, 2,5-diodobenzotrifluoride, 1,4-dichloro-2,3,5,6-tetrafluorobenzene, 1,4-dibromo-2,3,5,6-tetrafluorobenzene, 1,4-dibromo-2,3,5,6-tetrafluorobenzene, and 1,4-diodo-2,3,5,6-tetrafluorobenzene. Preferred among these compounds are p-dichlorobenzene, p-dimethylsulfonyloxybenzene, 2,5-dichlorotoluene, and 2,5-dichlorobenzotrifluoride.

Specific examples of the monomer (B) represented by the formula (6)' include 4,4'-dimethylsulfonyloxybiphenyl, 4,4'-dimethylsulfonyloxy-3,3'-dipropenylbiphenyl, 4,4'-dibromobiphenyl, 4,4'-diodobiphenyl, 4,4'-dimethylsulfonyloxy-3,3'-dimethylbiphenyl, 4,4'-dimethylsulfonyloxy-3,3'-difluorobiphenyl, 4,4'-dimethysulfonyloxy-3,3',5,5'-tetrafluorobiphenyl, 4,4'-dibromooctafluorobiphenyl, and 4,4'-methylsulfonyloxyoctafluorobiphenyl. Preferred among these compounds are 4,4'-dimethylsulfonyloxybiphenyl, 4,4'-dibromobiphenyl, and 4,4'-dimethylsulfonyloxy-3,3'-dipropenylbiphenyl.

Specific examples of the monomer (B) represented by the formula (7)' include m-dichlorobenzene, m-dibromobenzene, m-diodobenzene, m-dimethylsulfonyloxybenzene, 2,4-dichlorotoluene, 2,4-dibromotoluene, 2,4-diodotoluene, 3,5-dichlorotoluene, 3,5-dibromotoluene, 3,5-diodotoluene, 2,6-dichlorotoluene, 2,6-dibromotoluene, 2,6-diodotoluene, 3,5-dimethylsulfonyloxytoluene, 2,6-dimethylsulfonyloxytoluene, 2,4-dichlorobenzotrifluoride, 2,4-dibromobenzotrifluoride, 2,4-diodobenzotrifluoride, 3,5-dichlorobenzotrifluoride, 3,5-dibromotrifluoride, 3,5-diodobenzotrifluoride, and 1,3-dibromo-2,4,5,6-tetrafluorobenzene. Preferred among these compounds are m-dichlorobenzene, 2,4-dichlorotoluene, 3,5-dimethylsulfonyloxytoluene, and 2,4-dichlorobenzotrifluoride.

Among the monomers (B) represented by the formulae (5)' to (7)', dichlorobenzoic acid derivatives such as 2,5-dichloro-4'-phenoxybenzophenone, 2,4-dichloro-4'-phenoxybenzophenone, 2,5-dichloro-4'-phenoxyphenylbenzoate and 2,4-dichloro-4'-phenoxyphenylbenzoate are preferably used from the standpoint of solubility and polymerizability.

The copolymerization ratio of the monomer (1) represented by the formula (1) and at least one other monomer (monomer (A) to (B)) selected from the group consisting of aromatic compounds represented by the formulae (4)' to (7)' is the same as the ratio of the repeating structural unit (3) and the other repeating structural units. The proportion of the monomers (A) and (B) as other monomers are the same as that of the units (A) and (B).

The catalyst to be used in the production of the copolymer of the invention is a catalyst system containing a transition metal compound. This catalyst system comprises (i) a transition metal salt and ligands or a transition metal (salt) having ligands oriented therein and (ii) a reducing agent as essential components. This catalyst system may comprise a "salt" incorporated therein to raise the polymerization rate.

Examples of the transition metal salt employable herein include nickel compounds such as nickel chloride, nickel bromide, nickel iodide and nickel acetylacetonate, palladium compounds such as palladium chloride, palladium bromide and palladium iodide, iron compounds such as iron chloride, iron bromide and iron iodide, and cobalt compounds such as cobalt chloride, cobalt bromide and cobalt iodide. Particularly preferred among these transition metal salts are nickel chloride, and nickel bromide. Examples of the ligands employable herein include triphenyl phosphine, 2,2'-bipyridine, 1,5-cyclooctadiene, and 1,3-bis (diphenylphosphine)propane. Preferred among these ligands are triphenyl phosphine, and 2,2'-bipyridine. These ligands may be used alone or in combination of two or more thereof.

Examples of the transition metal (salt) having ligands oriented therein include nickel chloride bis (triphenylphosphine), nickel bromide bis(triphenyl phosphine), nickel iodide bis (triphenylphosphine), nickel nitrate bis(triphenylphosphine), nickel chloride (2,2'-bipyridine), nickel bromide (2,2'-bipyridine), nickel iodide (2,2'-bipyridine), nickel nitrate (2,2'-bipyridine), bis (1,2-cyclooctadiene) nickel, tetrakis (triphenylphosphine) nickel, tetrakis(triphenylphosphite), and tetrakis(triphenyl phosphine) palladium. Preferred among these compounds are nickel chloride bis (triphenylphosphine), and nickel chloride (2,2'-bipyridine).

Examples of the reducing agent to be used in the catalyst system of the invention include iron, zinc, manganese, aluminum, magnesium, sodium, and calcium. Preferred among these reducing agents are zinc, magnesium, and manganese. These reducing agents may be allowed to come in contact with an acid such as organic acid so that they can be further activated before use.

Examples of the "salt" to be used in the catalyst system of the invention include sodium compounds such as sodium fluoride, sodium chloride, sodium bromide, sodium iodide and sodium sulfate, potassium compounds such as potassium fluoride, potassium chloride, potassium bromide, potassium iodide and potassium sulfate, and ammonium compounds such as tetraethyl ammonium fluoride, tetraethyl ammonium chloride, tetraethyl ammonium bromide, tetraethyl ammonium iodide and tetraethyl ammonium sulfate. Preferred among these salts are sodium bromide, sodium iodide, potassiumbromide, tetraethyl ammonium bromide, and tetraethyl ammonium iodide.

Referring to the proportion of the various components of the catalyst system, the proportion of the transition metal salt or the transition metal (salt) having ligands oriented therein is normally from 0.0001 to 10 mols, preferably from 0.01 to 0.5 mols per mol of the total amount of the monomers. When the proportion of the transition metal (salt) falls below 0.0001 mols, the polymerization reaction cannot proceed sufficiently. On the contrary, when the proportion of the transition metal (salt) exceeds 10 mols, the resulting copolymer exhibits a reduced molecular weight.

In the case where the catalyst system comprises a transition metal salt and ligands, the proportion of the ligands is normally from 0.1 to 100 mols, preferably from 1 to 10 mols per mol of the transition metal salt. When the proportion of the ligands falls below 0.1 mols, the resulting catalytic activity is insufficient. On the contrary, when the proportion of the ligands exceeds 100 mols, the resulting copolymer has a reduced molecular weight.

The proportion of the reducing agent in the catalyst system is normally from 0.1 to 100 mols, preferably from 1 to 10 mols per mol of the total amount of the monomers. When the proportion of the reducing agent falls below 0.1 mols, the polymerization reaction cannot proceed sufficiently. On the contrary, when the proportion of the ligands exceeds 100 mols, the resulting polymer can difficultly be purified to disadvantage.

In the case where the catalyst system comprises a "salt", the proportion of the salt is normally from 0.001 to 100 mols, preferably from 0.01 to 1 mols per mol of the total amount of the monomers. When the proportion of the salt falls below 0.001 mols, the resulting effect of enhancing the polymerization rate is insufficient. On the contrary, when the proportion of the salt exceeds 100 mols, the resulting polymer can difficultly be purified to disadvantage.

Examples of the polymerization solvent employable herein include tetrahydrofurane, cyclohexane, dimethyl sulfoxide, N,N-dimethylformamide, N,N-dimethylacetamide, 1-methyl-2-pyrrolidone, γ-butyrolactone, and γ-butyrolactam. Preferred among these polymerization solvents are tetrahydrofurane, N,N-dimethylformamide, N,N-dimethylacetamide, and 1-methyl-2-pyrrolidone. The polymerization solvent is preferably dried thoroughly before use. The total concentration of the monomers in the polymerization solvent is normally from 1 to 90% by weight, preferably from 5 to 40% by weight.

The polymerization temperature at which the copolymer of the invention is produced is normally from 0° C. to 200° C., preferably from 50° C. to 80° C. The polymerization time is normally from 0.5 to 100 hours, preferably from 1 to 40 hours.

An example of the reaction formula by which a copolymer comprising repeating structural units (free of sulfonic acid group) represented by the formulae (3) and (4) is produced from the monomer (1) represented by the formula (1) and the monomer (A) represented by the formula (4)' will be given below.

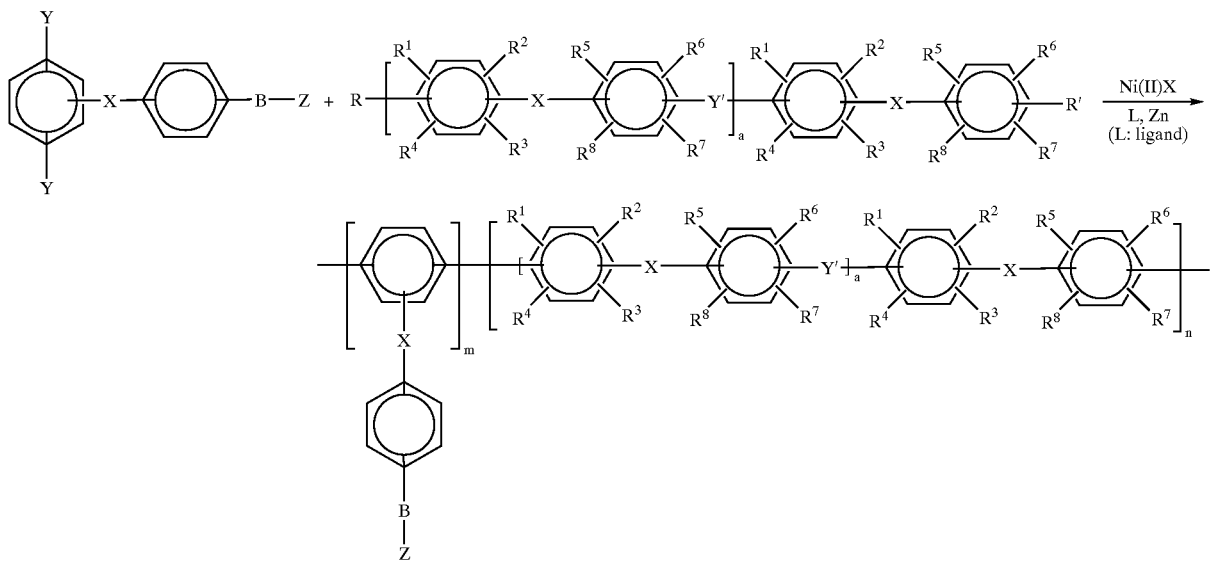

wherein m and n each represent the number of repeating structural units.

The structure of the copolymer of the invention can be confirmed by C—O—C absorption at a wavelength of from 1,230 to 1,250 cm$^{-1}$ and C=O absorption at a wavelength of from 1,640 to 1,660 cm$^{-1}$ on infrared absorption spectrum or by the peak of from 6.8 to 8.0 ppm corresponding to aromatic proton on nuclear magnetic resonance spectrum ($^1$H-NMR).

The copolymer containing a sulfonic acid group to be used in the conductive membrane of the invention can be obtained by incorporating a sulfonic acid group in the aforementioned copolymer free of sulfonic acid group using a sulfonating agent.

The incorporation of a sulfonic acid group can be accomplished, e.g., by subjecting the copolymer free of sulfonic acid group to sulfonation with a known sulfonating agent such as sulfuric anhydride, fuming sulfuric acid, chlorosulfonic acid, sulfuric acid and sodium hydrogensulfite under known conditions [Polymer Preprints, Japan, Vol. 42, No. 3, p. 730 (1993); Polymer Preprints, Japan, Vol. 42, No. 3, p. 736 (1994); Polymer Preprints, Japan, Vol. 42, No. 7, p. 2,490–2,492 (1993)].

In some detail, the sulfonation of the copolymer free of sulfonic acid group can be accomplished by reacting the copolymer free of sulfonic acid group with the aforementioned sulfonating agent in the absence or presence of solvent. Examples of the solvent employable herein include hydrocarbon solvents such as n-hexane, ether-based solvents such as tetrahydrofurane and dioxane, aprotic polar solvents such as dimethylacetamide, dimethylformamide and dimethyl sulfoxide, and halogenated hydrocarbons such as tetrachloroethane, dichloroethane, chloroform and methylene chloride. The reaction temperature is not specifically limited but is normally from −50° C. to 200° C., preferably −10° C. to 100° C. The reaction time is normally from 0.5 to 1,000 hours, preferably from 1 to 200 hours.

The content of the sulfonic acid group in the sulfonic acid group-containing copolymer thus obtained is from 0.5 to 3 mg equivalents/g, preferably from 0.7 to 2.8 mg equivalents/g. When the content of the sulfonic acid group falls below 0.5 mg equivalents/g, the resulting sulfonic acid group-containing copolymer does not exhibit a raised proton conductivity. On the contrary, when the content of the sulfonic acid group exceeds 3 mg equivalents/g, the resulting sulfonic acid group-containing copolymer exhibits an enhanced hydrophilicity and thus becomes a water-soluble polymer or exhibits a deteriorated durability, though not going so far as to become water-soluble.

The content of the sulfonic acid group can be easily adjusted by the copolymerized amount (composition) of the monomer (1) or the monomer (A) constituting the aromatic compound unit having an electron-withdrawing group and an electron-donative group in its main chain.

The molecular weight of the unsulfonated precursor of the sulfonic acid group-containing copolymer of the invention thus obtained is from 10,000 to 1,000,000, preferably from 20,000 to 800,000 as calculated in terms of weight average molecular weight in polystyrene equivalence. When the molecular weight of the precursor falls below 10,000, the resulting copolymer exhibits insufficient film forming properties causing the coating film to undergo cracking and have an insufficient strength. On the contrary, when the molecular weight of the precursor exceeds 1,000,000, the resulting copolymer exhibits an insufficient solubility and too high a solution viscosity to be worked fairly.

The structure of the sulfonic acid group-containing copolymer of the invention can be confirmed by S=O absorption at a wavelength of from 1,030 to 1,045 $cm^{-1}$, from 1,160 to 1,190 $cm^{-1}$ and C—O—C absorption at a wavelength of from 1,130 to 1,250 $cm^{-1}$ and C=O absorption at a wavelength of from 1,640 to 1,660 $cm^{-1}$ on infrared absorption spectrum. The composition ratio of these components can be determined by neutralization titration of sulfonic acid or elementary analysis. The structure of the sulfonic acid group-containing copolymer of the invention can be confirmed also by the peak of from 6.8 to 8.0 ppm corresponding to aromatic proton on nuclear magnetic resonance spectrum ($^1$H-NMR).

The proton-conductive membrane of the invention comprises the aforementioned sulfonic acid group-containing copolymer. The proton-conductive membrane of the invention may further comprise an inorganic acid such as sulfuric acid and phosphoric acid, an organic acid such as carboxylic acid, a proper amount of water, etc. besides the aforementioned sulfonic acid group-containing copolymer.

In order to produce the conductive membrane of the invention, the sulfonic acid group-containing copolymer of the invention may be dissolved in a solvent, and then subjected to casting method involving casting for making film or melt forming method. Examples of the solvent to be used in the casting method include aprotic polar solvents such as dimethylacetamide, dimethylformamide, N-methylpyrrolidone and dimethyl sulfoxide, and alcohol solvents such as methanol.

The conductive membrane of the invention can be used as a proton-conductive membrane for primary battery electrolyte, secondary battery electrolyte, fuel cell polymer solid electrolyte, display element, various sensors, signal transfer medium, solid capacitor, ion exchange membrane, etc.

The invention will be further described in the following examples, but the invention should not be construed as being limited thereto.

The various properties to be measured in the examples were determined in the following manner.

Weight Average Molecular Weight

For the determination of the weight average molecular weight of the unsulfonated precursor polymer, the molecular weight in polystyrene equivalence was measured with tetrahydrofuran (THF) as a solvent by gel permeation chromatography (GPC).

Sulfonic Acid Equivalent

The sulfonated polymer thus obtained was washed with water until the wash water became neutral so that remaining free acid was removed. The sulfonated polymer was thoroughly washed with water, dried, and then measured out in a predetermined amount. The sulfonated polymer was dissolved in a mixture of THF and water. The solution was then neutralized with a standard NaOH solution with phenolphthalein as an indicator. From the neutralization point, the sulfonic acid equivalent was determined.

Measurement of Proton Conductivity

For the measurement of a.c. resistivity, the a.c. impedance across platinum wires (diameter: 0.5 mm) pressed against the surface of a 5 mm wide strip-shaped film specimen kept in a constant temperature and humidity device was determined. In some detail, the impedance was measured at 10 kHz at a temperature of 85° C. and a relative humidity of 90%. As the resisitivity meter there was used a chemical impedance measurement system produced by NF Corporation. As the constant temperature and humidity device there was used JW241, produced by Yamato Chemical Co., Ltd. Five platinum wires were pressed against the surface of the test specimen at an interval of 5 mm. With the distance between the electrodes varied from 5 mm to 20 mm, the a.c. resistivity was measured. From the distance between wires and the resistivity gradient was then calculate the specific resistivity of the film. The reciprocal of the specific resistivity was then calculated to determine the a.c. impedance. From this impedance was then calculated the proton conductivity.

Specific resistivity ($\Omega \cdot cm$)=0.5 ($cm$)×film thickness ($cm$)×resistivity gradient between resistive wires ($\Omega/cm$)

Thermal Properties
Thermal Decomposition Temperature

The decomposition temperature of the sulfonated polymer measured by TGA (at a temperature rising rate of 20° C./min in a nitrogen atmosphere) was defined as thermal decomposition temperature.

Glass Transition Temperature:

The temperature at which the test specimen shows a heat capacity change by DSC (at a temperature rising rate of 20° C./min in a nitrogen atmosphere) was defined as glass transition temperature.

Tensile Strength

A strip-shaped film test specimen was prepared by forming a 50 μm thick film of sulfonated polymer having a size of 3 mm wide×65 mm long. Using a tensile testing machine, the test specimen was measured for elastic modulus, breaking strength and elongation.

Flexing Resistance

Using a flexing resistance testing machine, a 50 μm thick sulfonated polymer film was bent at a rate of 166 times/min, a load of 200 g and a flex deformation angle of 135°. Those which can be bent 500 or more times until they break are considered good.

Behavior in Hot Water

A film having a predetermined size was dipped in a 95° C. water for 5 hours. Those showing a dimensional change of less than 50% are considered good. Those showing a dimensional change of not smaller than 50% and remarkable swelling are considered poor.

SYNTEHSIS EXAMPLE

Synthesis of 2,5-dichloro-4'-(4-phenoxyphenoxy)-benzophenone (1) Synthesis of 2,5-dichloro-4'-fluorobenzophenone 461 g (4.80 mols) of fluorobenzene and 139 g (1.04 mols) of aluminum chloride were measured out in a three-necked flask equipped with a thermometer, a dropping funnel and a nitrogen intake pipe. The reaction system was then cooled to a temperature of about 10° C. while being stirred by means of a magnetic stirrer in a nitrogen atmosphere. Subsequently, 168 g (800 mmols) of 2,5-dichlorobenzoic acid chloride were gradually dropped into the reaction solution using a dropping funnel in about 1 hour. The resulting hydrogen chloride gas was introduced into a washing bottle containing a 5% solution of sodium hydroxide so that it was neutralized.

After 4 hours of dropping, little or no hydrogen chloride gas was produced. Thin layer chromatography (TLC) then showed that the starting material was consumed and indicated only a spot of product. Thus, it was confirmed that the reaction had been terminated. The reaction product was then poured into 320 g of an aqueous solution obtained by mixing concentrated hydrochloric acid and ice at a ratio of 1:10. The mixture was then stirred for about 1 hour.

The reaction solution was then extracted with ethyl acetate. An organic material was then separated using a separatory funnel. Subsequently, the organic phase was washed with a 5 wt % aqueous solution of sodium hydrogencarbonate, distilled water and then brine. The organic phase thus washed was then dried over anhydrous magnesium sulfate. The inorganic salt was then removed by filtration. The solvent was then distilled off to obtain a crude product. The crude product was then recrystallized from 480 g of a 1:7 mixture (by volume) of ethyl acetate and n-hexane to obtain a white crystal having a melting point of from 84° C. to 85° C. in a yield of 150 g (70%). The infrared absorption spectrum of 2,5-dichloro-4'-fluorobenzophenone thus obtained is shown in FIG. 1.

(2) Synthesis of 2,5-dichloro-4'-(4-phenoxyphenoxy)-benzophenone

The reaction formula by which this compound is synthesized is shown before.

Figure 2:
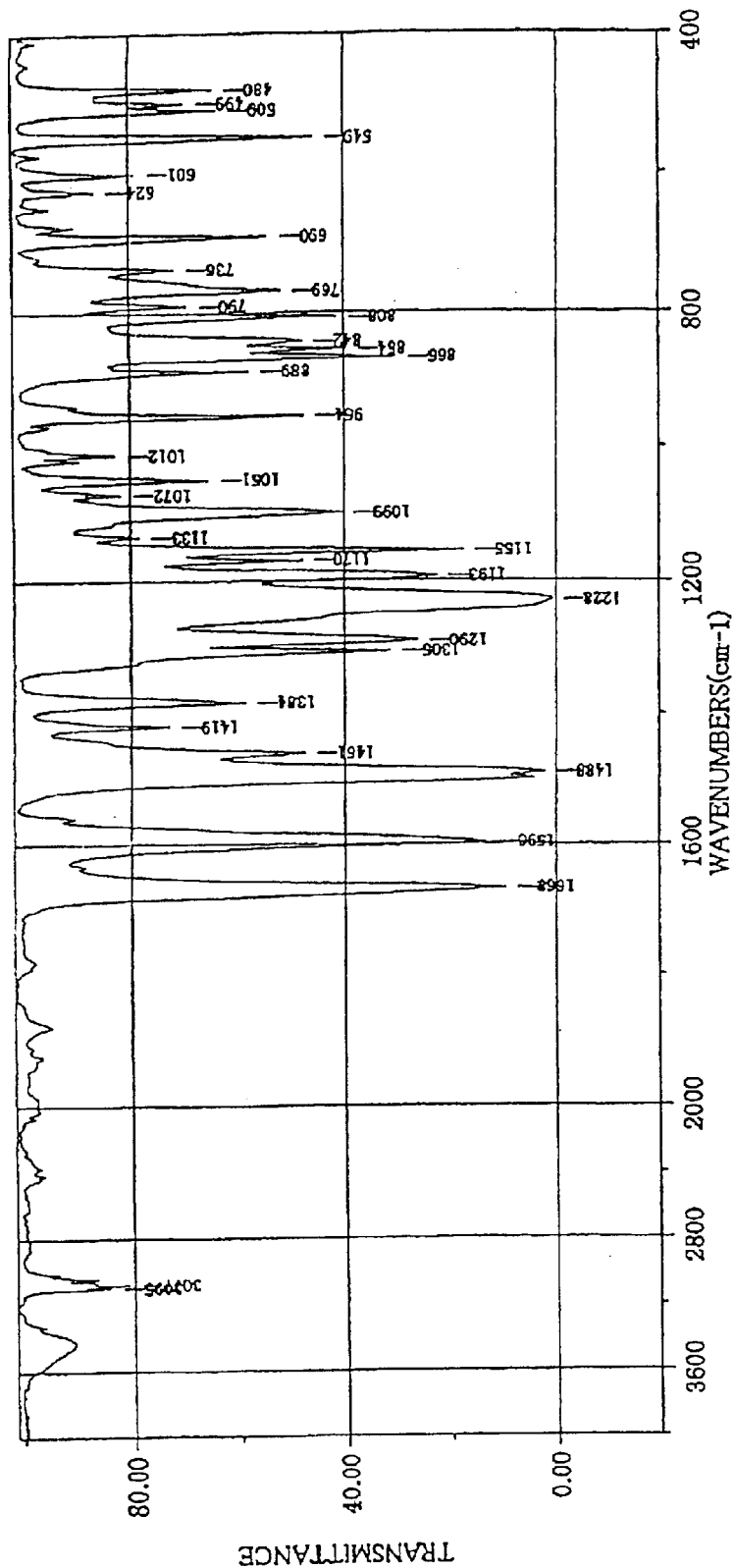
FIG. 2 is the infrared absorption spectrum of 2,5-dichloro-4'-(4-phenoxyphenoxy)benzophenone (monomer of the invention) obtained in Synthesis Example 1.
Figure 3:
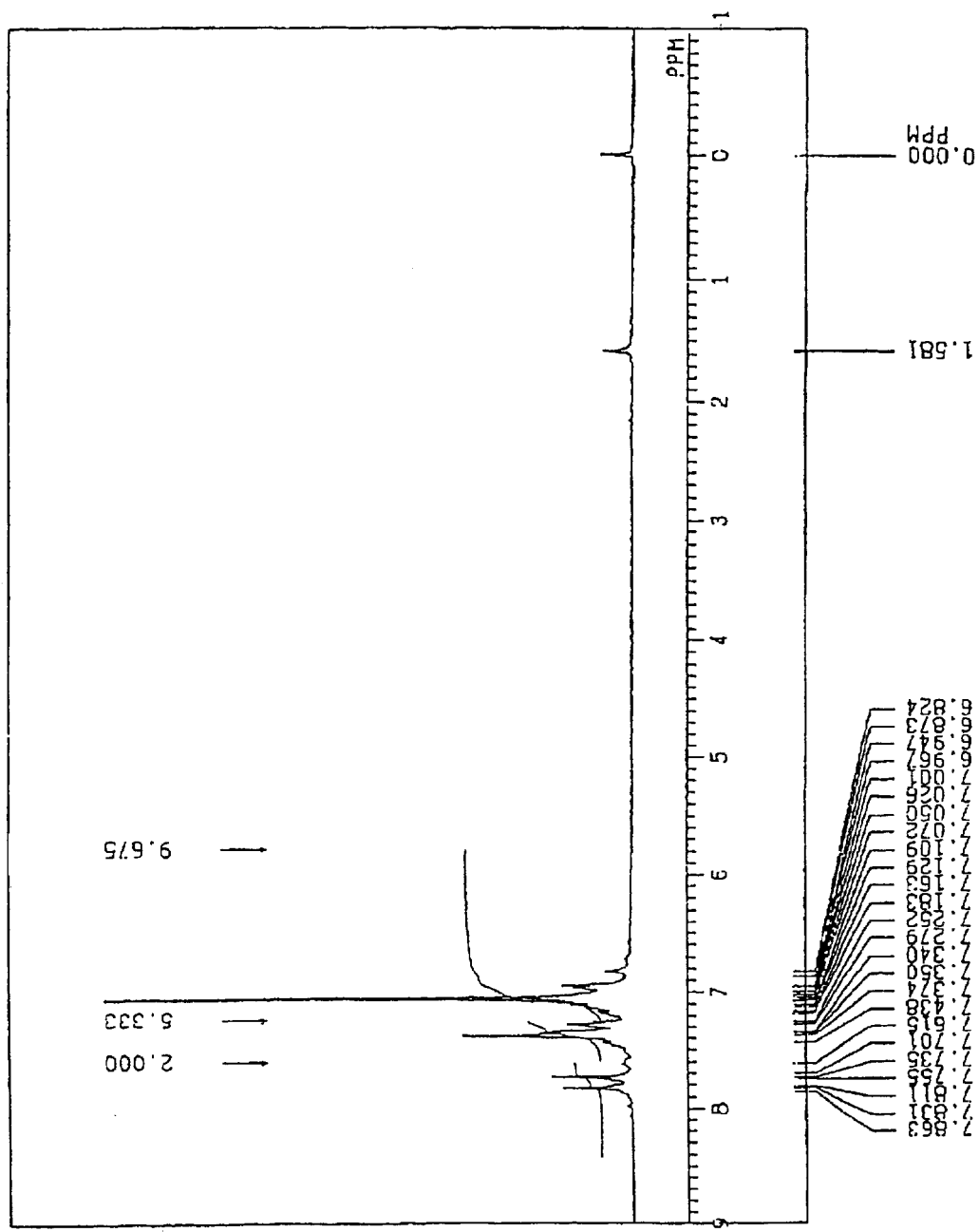
FIG. 3 is $^1$H-NMR spectrum of 2,5-dichloro-4'-(4-phenoxyphenoxy)benzophenone (monomer of the invention) obtained in Synthesis Example 1.

In some detail, 10.8 g (40.0 mmols) of 2,5-dichloro-4'-fluorobenzophenone (Compound (1)') synthesized in the process (1), 7.45 g (40.0 mmols) of 4-phenoxyphenol (Compound (1)") and 8.29 g (60 mmols) of potassium carbonate were measured out in a three-necked flask equipped with a Dean-Stark tube, a condenser and a thermometer. Into the mixture was then poured a mixture of 50.0 g of dimethylacetamide and 50.0 g of toluene. The reaction mixture was then stirred by means of a magnetic stirrer. The content of the flask was then heated to a temperature of 130° C. over an oil bath. The reaction solution was then heated under reflux while the resulting water was being removed from the reaction system through the Dean-Stark tube. When water was no longer produced, the content of the flask was then heated to a temperature of 150° C. while toluene was being removed from the reaction system. The content of the flask was then reacted for about 4 hours. When the termination of reaction was confirmed by TLC, the content of the flask was then allowed to cool to room temperature. After cooling, the content of the flask was then poured into water. The mixture was then stirred for about 1 hour. An organic material was then separated from the mixture using a separatory funnel. The organic material was then extracted with ethyl acetate. The phase thus extracted was washed with water and brine, and then dried over anhydrous magnesium sulfate. After drying, the inorganic salt was removed by filtration. The solvent was then distilled off to obtain a crude product. The crude product was then recrystallized from 96.0 g of a 1:5 (by volume) mixture of ethyl acetate and n-hexane to obtain a purified white crystal having a melting point of from 98° C. to 99° C. in an amount of 14.8 g (yield: 85%). The infrared absorption spectrum of Compound (1) thus obtained is shown in FIG. 2. $^1$H-NMR spectrum of Compound (1) is shown in FIG. 3.

EXAMPLE 1

131.86 g (303 mmols) of 2,5-dichloro-4'-(4-phenoxyphenoxy) benzophenone obtained in the Synthesis Example, 90.69 g (190 mmols) of 4,4'-bis(4-chlorobenzoylamino)diphenyl ether, 7.4 g (49 mmols) of sodium iodide, 7.4 g (11 mmols) of bistriphenylphosphine nickel dichloride, 29.8 g (113 mmols) of triphenyl phosphine and 494.4 g (760 mmols) of zinc were measured out in a three-necked flask equipped with a reflux condenser and a three-way cock. The flask was then dipped in a 70° C. oil bath. The air in the flask was then replaced by nitrogen. To the content of the flask was then added 1,000 ml of N-methyl-2-pyrrolidone in a nitrogen atmosphere to initiate polymerization reaction. After 20 hours of reaction, the reaction solution was then diluted with 500 ml of N-methyl-2-pyrrolidone. The polymerization solution was then poured into a drastically excess 1:10 mixture of hydrochloric acid and methanol to cause the precipitation of a polymer. The polymer thus precipitated was repeatedly washed and filtered to undergo purification, and then dried in vacuo to obtain a white powder in an amount of 174.4 g (yield: 93%). The product had a weight average molecular weight of 127,000. The polymer thus obtained was then formed into a film with N-methyl-2-pyrrolidone. The film thus formed was then dipped in methanol. The film was then observed to undergo no swelling.

To 150 g of the polyarylene copolymer thus obtained was then added 1,500 ml of concentrated sulfuric acid. The reaction mixture was then stirred. The reaction mixture was then allowed to undergo sulfonation reaction at room temperature for 24 hours. After reaction, the reaction product was then poured into a large amount of purified water to cause the precipitation of a sulfonated polymer. The polymer thus obtained was then repeatedly washed with water until the wash water became almost neutral, and then filtered to recover the sulfonated polymer which was then dried at a temperature of 90° C. in vacuo. The yield of the sulfonated polymer was 185.0 g.

EXAMPLE 2

The reaction procedure of Example 1 was followed except that the formulation of the monomers to be charged comprised 105.49 g (242 mmols) of 2,5-chloro-4'-(4-phenoxyphenoxy) benzophenone and 108.83 g (228 mmols) of 4,4'-bis(4-chlorobenzoylamino)diphenyl ether. As a result, a polymer was obtained in an amount of 170.1 g (yield: 94%). The polymer thus obtained had a weight average molecular weight of 144,000.

150 g of the polymer thus obtained was then subjected to sulfonation in the same manner as in Example 1 to obtain 178.4 g of a sulfonated polymer.

EXAMPLE 3

The reaction procedure of Example 2 was followed except that 108.83 g (228 mmols) of 4,4'-bis(4-chlorobenzoylamino) diphenyl ether was replaced by 108.83 g (228 mmols) of 3,4'-bis(4-chlorobenzoylamino)diphenyl ether. As a result, a polymer was obtained in an amount of 170.1 g (yield: 94%). The polymer thus obtained had a weight average molecular weight of 123,000.

150 g of the polymer thus obtained was then subjected to sulfonation in the same manner as in Example 1 to obtain 164.4 g of a sulfonated polymer.

EXAMPLE 4

The reaction procedure of Example 1 was followed except that 90.69 g (190 mmols) of 4,4'-bis(4-chlorobenzoylamino) diphenyl ether was replaced by 84.99 g (190 mmols) of 4,4'-bis(4-chlorobenzoyl)diphenyl ether. As a result, a polymer was obtained in an amount of 169.1 g (yield: 93%). The polymer thus obtained had a weight average molecular weight of 119,000.

150 g of the polymer thus obtained was then subjected to sulfonation in the same manner as in Example 1 to obtain 185.2 g of a sulfonated polymer.

EXAMPLE 5

The reaction procedure of Example 1 was followed except that 90.69 g (190 mmols) of 4,4'-bis(4-chlorobenzoylamino) diphenyl ether was replaced by 81.14 g (170 mmols) of 4,4'-bis(4-chlorobenzoylamino)diphenyl ether and 5.02 g (20 mmols) of 4,4'-dichlorobenzophenone. As a result, a polymer was obtained in an amount of 170.2 g (yield: 93%). The polymer thus obtained had a weight-average molecular weight of 130,000.

150 g of the polymer thus obtained was then subjected to sulfonation in the same manner as in Example 1 to obtain 188.8 g of a sulfonated polymer.

EXAMPLE 6

The reaction procedure of Example 5 was followed except that 81.14 g (170 mmols) of 4,4'-bis(4-chlorobenzoylamino) diphenyl ether and 5.02 g (20 mmols) of 4,4'-dichlorobenzophenone were replaced by 42.47 g (95 mmols) of 4,4'-bis(4-chlorobenzoyl)diphenyl ether and 23.85 g (95 mmols) of 4,4'-dichlorobenzophenone. As a result, a polymer was obtained in an amount of 153.4 g (yield: 94%). The polymer thus obtained had a weight average molecular weight of 120,000.

150 g of the polymer thus obtained was then subjected to sulfonation in the same manner as in Example 1 to obtain 173.4 g of a sulfonated polymer.

COMPARATIVE EXAMPLE 1

The polymerization reaction procedure of Example 1 was followed except that only 263.72 g (606 mmols) of 2,5-dichloro-4'-(4-phenoxyphenoxy)benzophenone was used. As a result, a polymer was obtained in an amount of 205.23 g (yield: 93%). The polymer thus obtained had a weight average molecular weight of 149,000. 150 g of the polymer thus obtained was then subjected to sulfonation in the same manner as in Example 1. However, the polymer was water-soluble and thus was not solidified in water. Thus, the polymer could not be recovered.

COMPARATIVE EXAMPLE 2

A commercially available perfluorosulfonic acid-based polymer (Nafion 112, produced by E. I. du Pont de Nemours and Company) was evaluated in the same manner as mentioned above. As a result, this polymer was found to have a low elastic modulus and a glass transition temperature of not higher than 100° C. and have problems in dynamic properties and heat resistance.

COMPARATIVE EXAMPLE 3

The polymerization reaction and sulfonation procedure of Comparative Example 1 was followed except that 263.72 g (606 mmols) of 2,5-dichloro-4'-(4-phenoxyphenoxy) benzophenone was replaced by 208.00 g (606 mmols) of 2,5-dichloro-4'-phenoxybenzophenone. The properties of the polymer thus obtained are set forth in Table 1. As can be seen in these results, the polymer thus obtained is disadvantageous in toughness and hot water resistance.

The polymers obtained in Examples 1 to 6 were each then dissolved in NMP in a concentration of 10% by weight. The solutions thus obtained were each casted onto a glass plate, and then dried at a temperature of 100° C. Eventually, the casted materials were each dried in vacuo to remove the solvent therefrom. Thus, films were formed. The properties of the polymers are shown in the Table below.

TABLE

| Example No. | Unsulfonated component in copolymer (mol-%) | Sulfonic acid equivalent (mg equivalent/g) | Proton conductivity S/cm | Thermal properties Td (° C.) | Tg (° C.) | Elastic modulus Gpa | Strength Mpa | Elongation (%) | Flexing resistance | Behavior in hot water |
|---|---|---|---|---|---|---|---|---|---|---|
| Example 1 | 39:A | 2.3 | 0.13 | >290 | >250 | 2.76 | 54 | 25 | G | G |
| Example 2 | 49:A | 2.0 | 0.10 | >290 | >250 | 2.98 | 56 | 35 | G | G |

TABLE-continued

| Example No. | Unsulfonated component in copolymer (mol-%) | Sulfonic acid equivalent (mg equivalent/g) | Proton conductivity S/cm | Thermal properties Td (°C.) | Thermal properties Tg (°C.) | Dynamic properties Elastic modulus Gpa | Dynamic properties Strength Mpa | Dynamic properties Elongation (%) | Flexing resistance | Behavior in hot water |
|---|---|---|---|---|---|---|---|---|---|---|
| Example 3 | 49:B | 2.0 | 0.08 | >290 | >250 | 2.87 | 48 | 45 | G | G |
| Example 4 | 39:C | 2.3 | 0.15 | >290 | >250 | 2.56 | 49 | 35 | G | G |
| Example 5 | 35:A 4:D | 2.2 | 0.14 | >290 | >250 | 2.54 | 58 | 65 | G | G |
| Example 6 | 20:C 20:D | 2.4 | 0.15 | >290 | >250 | 2.32 | 59 | 35 | G | G |
| Comparative Example 2 | — | 1.0 | 0.15 | >290 | <100 | 0.22 | 30 | 180 | G | G |
| Comparative Example 3 | — | 2.7 | 0.34 | >290 | >250 | 3.34 | 45 | 3 | P | P |

A: 4,4'-Benzoylaminodiphenyl ether chain
B: 3,4'-Benzoylaminodiphenyl ether chain
C: 4,4'-Benzoyldiphenyl ether chain
D: 4,4'-Benzophenone chain
G: Good
P: Poor The monomer containing an electron-withdrawing group and an electron-donative group of the invention can provide a polyarylene-based copolymer the amount of sulfonic acid group to be incorporated in which can be easily controlled. The sulfonic group-containing polyarylene-based copolymer thus obtained can act as a conductive membrane which exhibits a high proton conductivity over a wide temperature range, an excellent adhesivity to substrate and electrode, excellent dynamic properties and an excellent hot water resistance and is less subject to embrittlement due to sulfonation.

Accordingly, the sulfonic group-containing polyarylene-based copolymer of the invention can be used as a conductive membrane for primary battery electrolyte, secondary battery electrolyte, fuel cell polymer solid electrolyte, display element, various sensors, signal transfer medium, solid capacitor, ion exchange membrane, etc. and thus has an extremely great industrial significance.

While the invention has been described in detail and with reference to specific embodiments thereof, it will be apparent to one skilled in the art that various changes and modifications can be made therein without departing from the spirit and scope thereof.

What is claimed is:

1. A monomer comprising an electron-withdrawing group and an electron-donative group represented by the following formula (1):

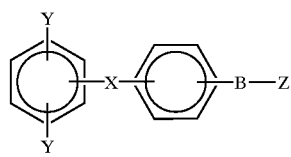

(1)

wherein Y represents a iodine atom, chlorine atom or bromine atom; X represents an electron-withdrawing group; B represents an electron-donative group; and Z represents a group represented by the following formula (2-1) or (2-2) or a monovalent condensed ring hydrocarbon group:

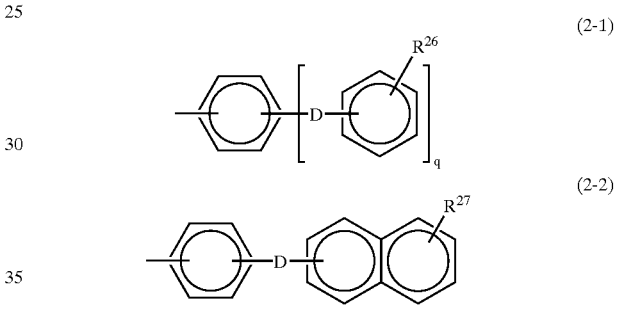

(2-1)

(2-2)

wherein D represents an electron-donative group or single bond; $R^{26}$ and $R^{27}$ each represent a hydrogen atom, alkyl group or aryl group; and q represents an integer of from 1 or 2.

2. The monomer comprising an electron-withdrawing group and an electron-donative group as claimed in claim 1, wherein said monomer represented by the formula (1) is 2,5-dichloro-4'-(4-phenoxyphenoxy)benzophenone.

3. A copolymer comprising a repeating structural unit represented by the general formula (3) in an amount of from 5 to 95 mol % and having a weight average molecular weight of from 10,000 to 1,000,000:

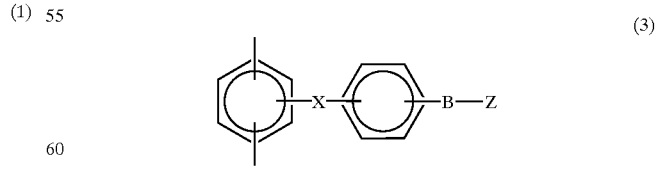

(3)

wherein X represents an electron-withdrawing group; B represents an electron-donative group; and Z represents a group represented by the following formula (2-1) or (2-2) or a monovalent condensed ring hydrocarbon group:

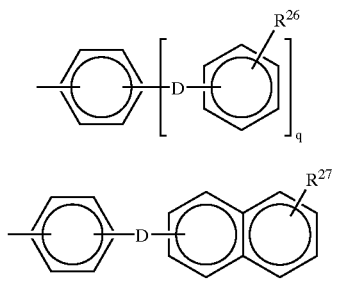

(2-1)

(2-2)

wherein D represents an electron-donative group or single bond; $R^{26}$ and $R^{27}$ each represent a hydrogen atom, alkyl group or aryl group; and q represents an integer of from 1 or 2.

4. The copolymer as claimed in claim 3, further comprising a repeating structural unit having a flexible structure in its main chain other than the repeating structural unit represented by the formula (3) in an amount of from 5 to 95 mol %.

5. The copolymer as claimed in claim 3, further comprising a sulfonic acid group in an amount of from 0.5 to 3 mg equivalents/g.

6. A proton-conductive membrane comprising a copolymer containing a sulfonic acid group as claimed in claim 5.

7. The copolymer as claimed in claim 4, further comprising a sulfonic acid group in an amount of from 0.5 to 3 mg equivalents/g.

8. A proton-conductive membrane comprising a copolymer containing a sulfonic acid group as claimed in claim 7.

9. A polymer comprising a repeating structural unit represented by the general formula (3) having a weight average molecular weight of from 10,000 to 1,000,000:

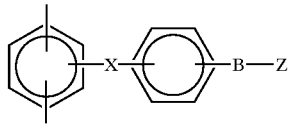

(3)

wherein X represents an electron-withdrawing group; B represents an electron-donative group; and Z represents a group represented by the following formula (2–1) or (2–2) or a monovalent condensed ring hydrocarbon group:

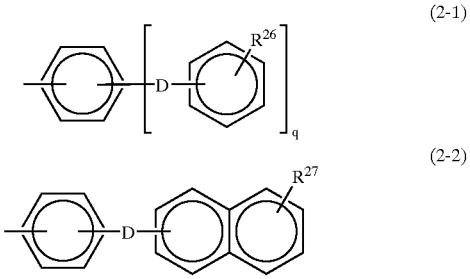

(2-1)

(2-2)

wherein D represents an electron-donative group or single bond; $R^{26}$ and $R^{27}$ each represent a hydrogen atom, alkyl group or aryl group; and q represents an integer of from 1 or 2.

10. The copolymer as claimed in claim 9, further comprising a sulfonic acid group in an amount of from 0.5 to 3 mg equivalents/g.

11. A proton-conductive membrane comprising a copolymer containing a sulfonic acid group as claimed in claim 10.

12. The polymer as claimed in claim 9, further comprising a repeating structural unit having a flexible structure in its main chain other than the repeating structural unit represented by the formula (3) in an amount of from 5 to 95 mol%.

13. The copolymer as claimed in claim 12, further comprising a sulfonic acid group in an amount of from 0.5 to 3 mg equivalents/g.

14. A proton-conductive membrane comprising a copolymer containing a sulfonic acid group as claimed in claim 13.

\* \* \* \* \*